United States Patent [19]

Humphrey

[11] Patent Number: 4,676,239

[45] Date of Patent: Jun. 30, 1987

[54] ANESTHETIC SYSTEM

[76] Inventor: David Humphrey, 222 Chelmsford Road, Durban, South Africa

[21] Appl. No.: 887,604

[22] Filed: Jul. 17, 1986

Related U.S. Application Data

[63] Continuation of Ser. No. 615,322, May 30, 1984, abandoned, which is a continuation of Ser. No. 298,820, Sep. 2, 1981, abandoned.

[30] Foreign Application Priority Data

Sep. 20, 1980 [ZA] South Africa .............. 80/541

[51] Int. Cl.$^4$ ................................ A61M 16/00
[52] U.S. Cl. .......................... 128/205.17; 128/911; 128/203.28; 128/910
[58] Field of Search ............. 128/203.11, 685, 203.29, 128/203.12, 203.28, 204.28, 205.24, 204.19, 910, 911, 203.14, 205.12, 205.13, 205.17, 205.19, 204.24; 55/DIG. 35

[56] References Cited

U.S. PATENT DOCUMENTS

| 2,006,878 | 7/1935 | Bandoly | 128/685 |
| 3,670,720 | 6/1972 | Panzer | 128/685 |
| 3,800,793 | 4/1974 | Marrese et al. | 128/910 |
| 3,814,092 | 6/1974 | Simionescu et al. | 128/203.28 |
| 3,901,230 | 8/1975 | Henkin | 128/910 |
| 3,993,059 | 11/1976 | Sjostrand | 128/205.24 |
| 4,007,736 | 2/1977 | Schreiber | 128/204.24 |
| 4,232,667 | 11/1980 | Chalon et al. | 128/203.28 |
| 4,249,527 | 2/1981 | Ko et al. | 128/205.17 |
| 4,281,652 | 8/1981 | Miller | 128/205.24 |

FOREIGN PATENT DOCUMENTS

2029703  3/1980  United Kingdom ........... 128/205.24

Primary Examiner—Richard J. Apley
Assistant Examiner—H. Macey
Attorney, Agent, or Firm—Ladas & Parry

[57] ABSTRACT

An anaesthetic system comprising, (a) inspiratory low pressure fresh gas supply tube adapted to receive low pressure gas and adapted for attachment of a reservoir bag tube and having a valve for control of gas to and from the reservoir bag (b) an expiratory tube comprising: (i) a valve to open or close the tube to permit from free up to totally restricted flow of gases in and out of the expiratory tube and (ii) a relief valve to permit gases to exit when pressure in the expiratory tube exceeds a predetermined value (c) the inspiratory and expiratory tubes communicating with a patient's face piece and being substantially free of restricted flow of gases whereby a universal mode of anaesthetic administration to a patient can be achieved.

1 Claim, 8 Drawing Figures

ANESTHETIC SYSTEM

This is a continuation of copending application Ser. No. 615,322 filed on May 30, 1984, now abandoned which is a continuation of Ser. No. 298,820 filed Sept. 2, 1981, now abandoned.

BACKGROUND OF THE INVENTION

The term "anaesthetic system" or anaesthetic breathing system, when used in this specification, is taken to mean the connecting apparatus between the anaesthetic machine and the face mask or endotracheal tube which connects to a patient, except where the context indicates otherwise.

Anaesthetic breathing systems are classified into 3 main groups, namely those which employ a circle system in which anaesthetic gases are reused by removing carbon dioxide due to circulation through a container containing soda lime (or similar substance); those which do not recycle gases and vent all expired gases to the atmosphere and do not permit any rebreathing by the use of two unidirectional valves in the inspiratory and expiratory side of the system; and those which do not recycle gases but vent expired gases to the atmosphere but nevertheless permit a degree of rebreathing. Of the last group all requirements for the administration of anaesthesia can be met with a number of different breathing systems, each having its own special application. Mapleson generally classified these systems as A, B, C, D and E and various analyses by research anaesthetists have revealed Mapleson A systems to be generally efficient for spontaneous respiration in adults, D systems to be generally efficient for controlled ventilation in adults and children and E systems to be advantageous though not necessarily efficient in children for both spontaneous and controlled ventilation. Systems B and C offered no special advantage at all. Hence to cover all eventualities encountered by the anaesthetist, Mapleson A, D and E systems are employed. Examples of Mapleson systems are the well known Magill (Mapleson A), the Bain (Mapleson D/E) and Ayre's T-piece (Mapleson E).

The Mapleson A or Magill system, is used for spontaneous respiration on adults and comprises a flexible tube delivering fresh gas from the machine, a reservoir bag at the machine end, and a pop-off valve, which is a simple relief valve, adjacent the patient's face. For controlled ventilation on adults, the Mapleson D/E or Bain system is used. This system comprises a fresh gas supply tube located within the bore of an expired gas removal tube at the distal end of which is located a relief valve and reservoir bag. Expired gases may be collected at the relief valve and removed from the theatre. The reservoir bag can be removed to allow connection to an automatic ventilator from which the expired gases may be removed from the theatre. In pediatrics, a simple T-piece (Mapleson E) is generally used for spontaneous respiration and controlled ventilation.

It is clear that each particular system is of limited application. In addition, the Magill and the T-piece systems contribute to the atmospheric pollution of the theatre by the introduction of expired respiration products and anaesthetic gas into the theatre at a point close to the patient from where it is cumbersome and inconvenient to attach a scavenging device. Only the Bain system allows easy scavenging back at the anaesthetic machine and removal of these gases out of the theatre with consequent reduction of this hazard.

A later system, based on the Mapleson A principle and developed by Lack, addressed the problem of theatre pollution by the provision of a take-off tube for expired gases coaxially down the fresh gas supply tube. The take-off tube exits from the bore of the supply tube at a location remote from the patient where a relief valve is arranged to blow off when the expiration pressure of the patient overcomes the resistance of the valve mechanism. The Lack system can only be used in the same situations as the Magill.

Recent attempts have been made to design an anaesthetic system which will have universal efficient use. Combination of a circle system used for spontaneous respiration and a Mapleson D system for controlled ventilation still limit its use to adults and requires soda lime with all its consequent disadvantages familiar to those skilled in the art. Another idea has been to use a closed loop without soda lime in which the separation of dead space gas (gas which has entered the lung but never reaches the respiratory gas exchange areas; it therefore has the same composition as fresh anaesthetic gas) from alveolar gas (which contains carbon dioxide exchanged from blood in the deeper parts of the respiratory passages) is achieved by a one-way valve on the expiratory limb immediately adjacent to the patient's face with two expiratory tubes from this valve to the anaesthetic machine. One tube carries dead space gas back to the beginning of the inspiratory limb thus completing the loop, while the other expiratory tube carries the alveolar gases to a pop-off valve from which these gases are vented from the system. A back-pressure mechanism on this valve permits controlled ventilation with the ventilator placed with the inspiratory limb of the loop. This device is not suitable for children because of its bulk and high airway resistance due to its complexity with the presence of a valve. Yet another approach to preserve dead space gas has been the introduction of a jet fluid control device at the patient end of a breathing system. This narrow jet directs the first gas to be expired (dead space gas) at a high velocity back down the inspiratory limb. As the pressure of gases rises in this limb, so the remainder of the expired gas (alveolar) is forced into the expiratory limb which is open to atmosphere at the anaesthetic machine. This, however, proved to function less efficiently than conventional systems, for the jet created such high turbulence within the system that it effectively mixed both dead and alveolar gas with the total loss of the former which now contained carbon dioxide. In conclusion not one multipurpose anaesthetic breathing system exists that is efficient and can be used for all patients irrespective of age.

Applicant is aware of the following U.S. Pat. Nos. 3,901,230 (Henkin) which relates to a closed loop system without the use of soda lime already described above; 4,281,652 (Miller) which relates to a jet fluid control device at the patient end of a breathing system also referred to above; 3,993,059 (Sjostrand) which relates to a high frequency positive ventilation system; 3,814,092 (Simionescu et al) which relates to a portable anaesthetic machine; 4,007,736 (Schreiber) which describes a ventilator with a timing mechanism and 4,249,527 (Ko et al) which relates to a pressure administrating apparatus which maintains a positive pressure in the lungs of a patient, and United Kingdom Patents Nos. 734,639 (Svenska Aktiebolaget Grasaccumulator) which relates to a closed and open circuit anaesthetic system and 1,272,583 (Blease Medical Equipment) which describes a ventilating machine designed to facilitate sterilization after use.

It is an object of this invention to provide a system which will find application in each and all of the circumstances mentioned above and which will, moreover, be as efficient, or considerably more efficient, than the systems presently in use in some or all of the applications referred to.

It is further the object of this invention to facilitate the scavenging of waste expired anaesthetic gases in all the applications mentioned above, thus reducing theatre pollution and its consequent danger to theatre staff to minimal levels or even eliminating pollution completely.

Yet another object of this invention is to provide an anaesthetic breathing system suitable for anaesthesia administration in both the sophisticated academic environment and remote rural areas. By virtue of the properties of the apparatus the anaesthetist can use very economical anaesthetic gas flows even without carbon dioxide absorption and yet he does not prejudice the safety of his patient. He can predict the carbon dioxide tension of this patient during controlled ventilation even when the latter is performed by hand. The invention is robust, simple and easily sterilized and consequently has many advantages over the circle absorber system which, unless specially adapted, is also unsuitable for children.

Yet another object of this invention is to provide an apparatus which is cheaper, easier to use, and less bulky than a combination of currently used anaesthetic breathing systems required for anaesthesia in the four circumstances mentioned earlier. Further this invention eliminates the use of soda lime and thus also the cost, transportation and the difficulties often encountered in remote areas in obtaining it.

SUMMARY OF THE INVENTION

According to the invention there is provided an anaesthetic system including a fresh gas supply tube, a reservoir bag connected thereto through a valve, and an expiratory tube having one or two outlets controlled by adjustable means. The arrangement of the invention permits a wide variety of applications for adult and child, spontaneous and controlled ventilation circumstances.

In one form of the invention the expiratory tube is provided with two outlets, a first outlet being controlled by a plug valve and a second outlet downstream of the first outlet being controlled by a relief valve which may be adjustable or a pop-off valve.

In another form of the invention the expiratory tube has a second outlet controlled by a screw-down type valve.

In both of these forms of the invention the port connecting the fresh gas supply tube to the reservoir bag may be controlled by a plug valve.

The fresh gas supply tube and the expiratory tube may be coaxial and the outlet is preferably located at a position remote from the patient end of the system.

Some embodiments of the invention are shown in the accompanying drawings which are partly diagrammatical representations of an anaesthetic system according to the invention.

DESCRIPTION OF PREFERRED EMBODIMENT

The anaesthetic system 10 shown in FIG. 1 comprises a fresh gas supply tube 12 or inspiratory tube connected to the anaesthetic machine at inlet 11, the patient end of which consists of flexible tubing, and an expired gas removal tube 14, or expiratory tube, which runs down the bore of the fresh gas supply tube 12 and exits therefrom at a location remote from the patient. The expired gas removal tube 14 terminates at the upper end thereof in a secondary outlet 30 controlled by a relief valve 16 which is a simple pop-off or screw-down device. A primary outlet 26 upstream of the secondary outlet 30 has a manually operable valve 18 controlled by a lever 19; rotation of valve 18 by lever 19 directs the flow of expired gas either to the primary outlet 26 or the secondary outlet 30. A second manually operable valve 20 controlled by a lever 21 is located in the fresh gas supply tube 12 to open or close a port 28 to a reservoir bag 22. Both valves 18, 20 may be plug valves located within the tubes, with a central bore disposed co-axially with the principal axis of the tube, each arranged to close their outlets or ports in one position of the levers 19, 21 and in the other position of the levers 19, 21 to open the outlet 26 or port 28. The pop-off valve 16 is a simple spring-loaded valve with a screw cap which can be screwed in to close the valve 16. At the junction of the primary and secondary outlets at valve 18 a cap 31 prevents expired gases from escaping from the system.

This cap may be removed to allow attachment of other outlets or anaesthetic devices such as a pressure release device or soda lime canister.

A face piece connector 24 is shown attached to the patient end of the fresh gas supply tube 12. The expired gas removal tube 14 stops short of the end of the fresh gas supply tube and is supported therein by a set of radially extending vanes (not shown).

In use the settings of the valves 16, 18, 20 will vary depending on the application of the system 10.

Figures 1A, 1B:
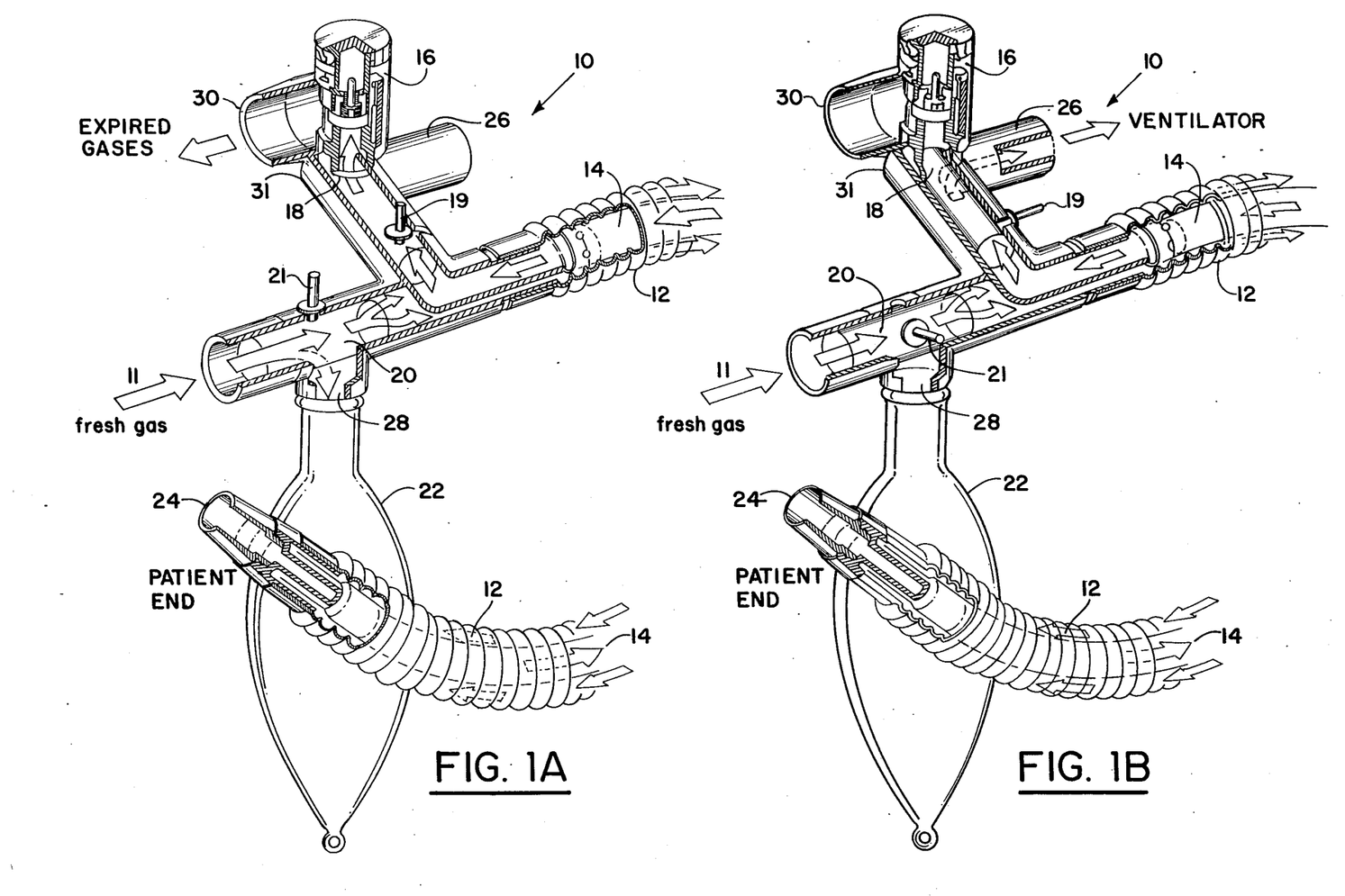
FIG. 1 is a perspective view of the invention partly in section, showing coaxial tubing and two functional positions of levers in FIGS. 1a and 1b, as well as the respective pathways for anaesthetic gases.

For adult spontaneous respiration the system 10 is used in a Mapleson A configuration (FIG. 1a). Valve 20 is opened by lever 21 thereby including the reservoir bag 22 in the circuit, and the outlet valve 18 is open to the relief valve 16 and closed to outlet 26. In this configuration the system can be regarded as a Lack system, fresh gas filling the reservoir bag 22 on the inspiratory limb and passing down the outer tube 12. Expired gases are vented by the inner tube 14 and exhausted through the pop-off valve 16 to be scavenged at the outlet 30.

Those skilled in the art of anaesthesia will appreciate that the function of the system is such that dead space gas can be efficiently preserved by the following means. At the beginning of inspiration the fresh gas supplied into the system from the anaesthetic machine has filled the reservoir bag. This collapses during inspiration, relief valve 16 remaining closed and preventing inhalation of alveolar gas from the expiratory limb. During exhalation initially exhaled dead space gas will flow back into the inspiratory limb as the pressure to lift the expiratory valve is higher than that which exists within the collapsed reservoir bag in the inspiratory limb. In mid-expiration the pressure in the inspiratory limb now exceeds that needed to open the valve 16 which consequently results in the elimination of the remainder of the exhaled gas (now of alveolar composition) down the expiratory limb and out through valve 16 and outlet 30. At this point a scavenging device (not shown) is attached to conduct gases out of the operating theatre. During clinical trials the applicant found this system to be more efficient than the traditionally used Magill Mapleson A system and to require a fresh gas flow of only 50 ml.kg$^{-1}$.min$^{-1}$.

During this test, the applicant found that the system 10, even with a fresh gas flow of only 50 ml.kg$^{-1}$.min$^{-1}$ performed as efficiently as the Magill (Mapleson A system) with a fresh gas flow of 70 ml.kg$^{-1}$.min$^{-1}$.

To change the system 10 for controlled ventilation in both children and adults, the reservoir bag 22 is functionally excluded from the circuit by means of the valve 20 by rotating lever 21 (FIG. 1b). A ventilator is connected by means of a tube to primary expiratory outlet 26 while valve 18 is opened to this outlet by rotating lever 19. Fresh gas flows directly to the patient via the supply tube 12 and expired gas exits freely through the valve 18 and outlet 26 to the ventilator.

The system now functions as a modified Mapleson E system. Those skilled in the art will appreciate that the ventilator attached to the expiratory limb merely functions as a piston. A preset volume of gas is intermittently forced into the expiratory limb thus driving expired gas back towards the patient's lungs. However since fresh anaesthetic gas is continually being introduced into the system at inlet 11 down the supply tube 12, this will displace exhaled gas down the expiratory tube 14 such that when the ventilator functions with each breath it is predominantly fresh gas that is pushed into the patient's lung and not expired gas. The ventilator gas therefore never actually reaches the patient and is further prevented from doing so by a tube of adequate volume attached between the outlet 26 and the ventilator. Consequently the ventilator can use atmospheric air as the "piston" gas without affecting the supply of anaesthetic gases to the patient. All exhausted gases are collected from the expiratory valve of the ventilator and conducted out of theatre.

For controlled ventilation clinical trials have confirmed that the system functions as a modified Mapleson D or E system. Like the Bain (which is also a modified Mapleson D system) normocarbia can be maintained with hyperventilation and a fresh gas flow of 70 ml.kg$^{-1}$.min$^{-1}$.

Manual ventilation is effectively achieved in the Mapleson A mode as for spontaneous respiration (FIG. 1a). The reservoir bag 22 is squeezed while the expiratory relief valve 16 is tightened to control the outflow of gas which is subsequently removed by scavenging. The applicant has found this method to be very efficient in marked contrast to the teachings for the alternative Magill Mapleson A system.

It will be appreciated by those skilled in the art that the switch from spontaneous or manual ventilation to controlled ventilation with an automatic ventilator simply involves the appropriate positions of levers 19 and 21 described above for each technique. By including or excluding the reservoir bag 22, the system 10 can be quickly converted from a Mapleson D system to an A or vice versa. Unlike any other system and in particular the Bain, the ventilator can remain attached at all times, the valve 16 does not need adjustment nor does the reservoir bag 22 need to be removed. Scavenging is always easily effected away from the patient in all modes of use either at outlets 30, 26 or at the ventilator.

For spontaneous respiration in paediatric anaesthesia, the system 10 may be in a "valveless" Mapleson A mode, a system that, in the experience of the applicant, is two or three times more efficient than the valveless but traditionally used T-piece of Mapleson E system.

The system functions much as the spontaneous respiration mode for adults (FIG. 1a) but with the following exceptions: fresh gas fills a smaller inspiratory reservoir bag 22 of 1 liter (or less), in place of the adult 2 liter bag. Expired alveolar gases pass along the inner tube 14, but instead of being exhausted, as with adults, through the pop-off valve 16, valve 18 is opened by the lever 19 to the main outlet 26 to allow gas to escape freely without passing through the pop-off valve. Dead space gas is not so well preserved since it can flow down both inspiratory and expiratory tubes at the beginning of expiration but nevertheless it has been found that the system is twice as efficient as the T-piece. Exhaust gases are scavenged at outlet 26 and conducted out of the theatre.

Recent physiological studies of the respiratory changes under anaesthesia have indicated that in children an increase in airway pressure may actually help gas exchange contrary to previous belief. This can be achieved by the inclusion of an expiratory resistance, a valve or flow resistor at the distal end of the expiratory limb of the breathing system. If this is desired with this invention, then valve 16 can be included by rotating valve 18 to the appropriate position as in FIG. 1a, exhaust gases being scavenged at outlet 30. This arrangement is functionally similar to that recommended for adults and is particularly efficient for it required one third of the fresh gas necessary for the T-piece to prevent breathing, an observation which was noted consistently during trials done by the applicant on children breathing spontaneously. It has been found that system 10 requires a maximum fresh gas flow of about 3.5 liters/min for spontaneous respiration in children, compared to 10.9 liters/min with the T-piece.

For controlled ventilation in children the system 10 is used as a Bain (modified Mapleson D) system as described earlier for adults and in FIG. 1b. A fresh gas flow of 3 liters min$^{-1}$ has been shown to maintain normocarbia or mild hypocarbia.

The resistance to expiration of the system 10 in the valveless Mapleson A mode has been found to be remarkably low. It had a resistance of less than half that of 40 Magill systems tested, while for paediatric use it also offered some 50% less resistance than the T-piece.

OTHER EMBODIMENTS

Attention is now drawn to FIGS. 2 to 8. Each of these alternative embodiments of the invention retain the same functional characteristics as the preferred embodiment, and can be used with adults and children for both spontaneous and controlled ventilation. It will be observed that for spontaneous respiration for adults and children each embodiment allows for inclusion of a reservoir bag on the inspiratory limb and a relief valve on the expiratory limb, while for controlled ventilation for adults and children the invention allows exclusion of the reservoir bag on the inspiratory limb and for attachment of a ventilator to the expiratory limb. Compared to FIG. 1 like components retain the same last two digits.

Figure 2A:
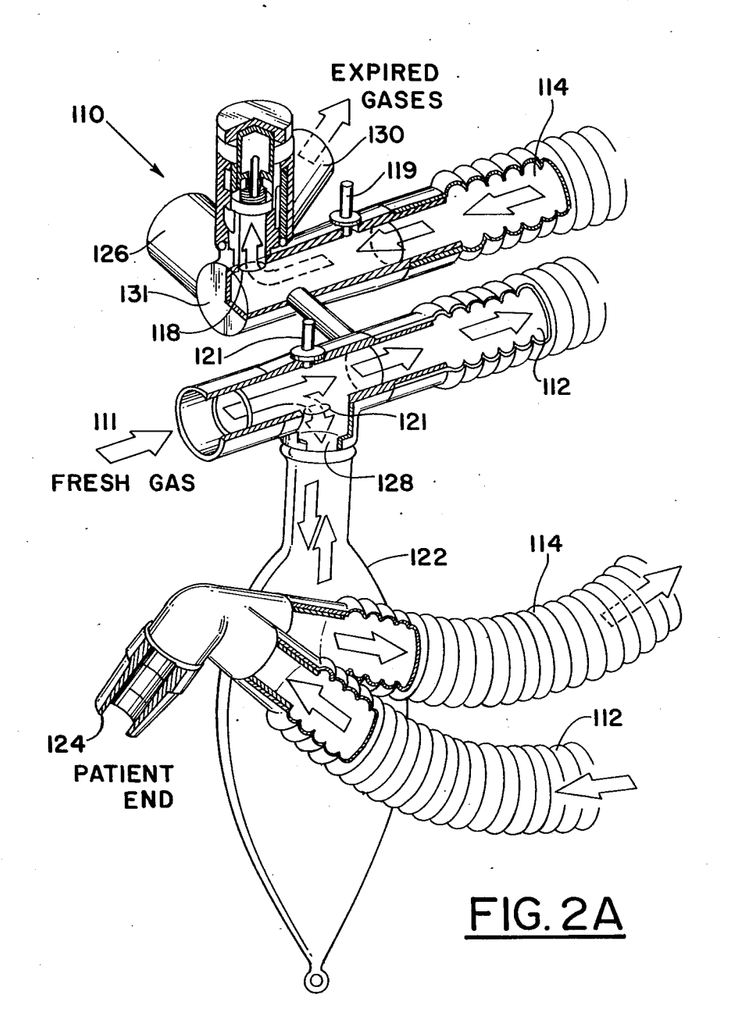
FIG. 2 is a perspective view of the invention partly in section, showing parallel tubing and two functional positions of levers 119 and 121 in FIGS. 2a and 2b, as well as the respective pathways for anaesthetic gases.
Figure 2B:
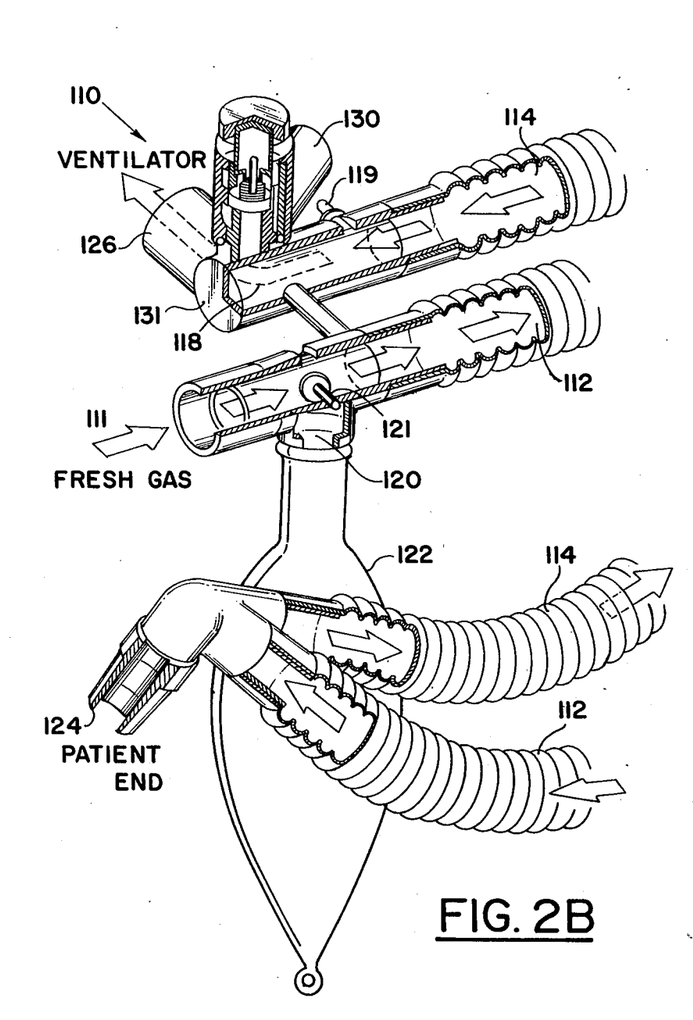

In FIG. 2 system 110 is similar to system 10 of FIG. 1 except that the system 110 is shown with the inspiratory tube 112 (12 in FIG. 1) and expiratory tube 114 (14 in FIG. 1) running parallel and not coaxial. All other components are identical. A bridge 133 holds the two limbs together at the patient end; it has no other function and does not carry gas between the limbs. Lever settings are identical to those described for the preferred embodiment of FIG. 1.

Figure 3A:
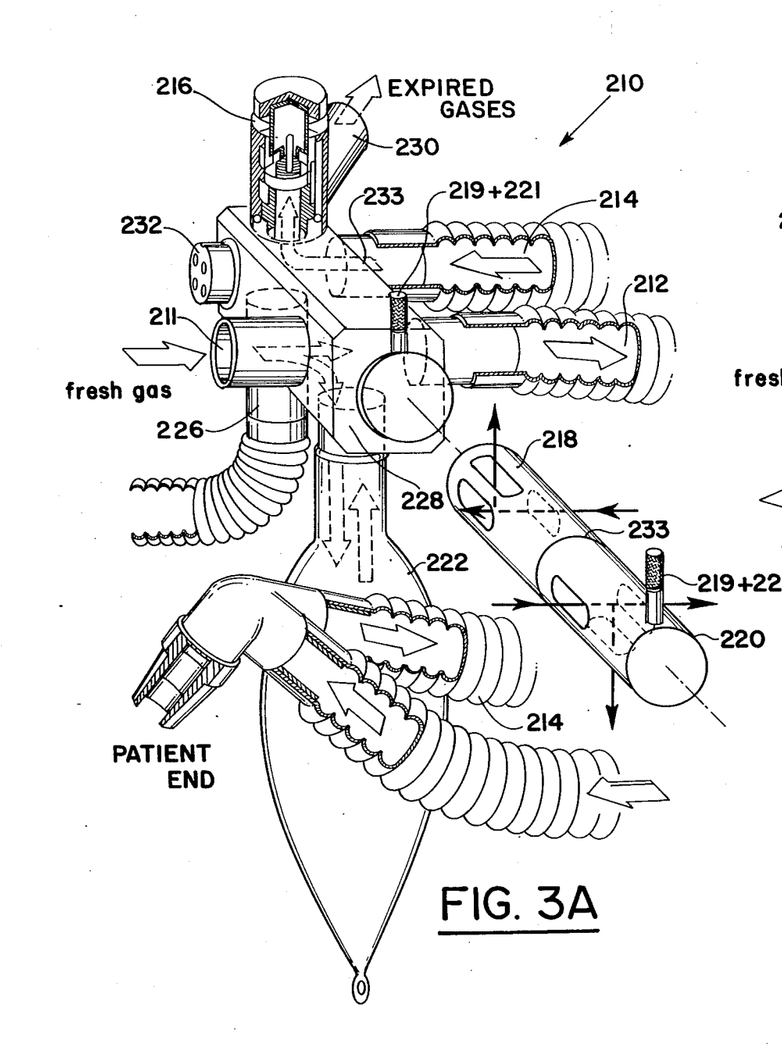
FIG. 3 is a perspective view of the invention partly in section view, showing parallel tubing and the two levers as a single lever. The respective functional positions of this lever are shown in FIGS. 3a and 3b, as are the respective pathways for anaesthetic gases. An exploded view of the rotating valve mechanism controlled by the lever is also shown.
Figure 3B:
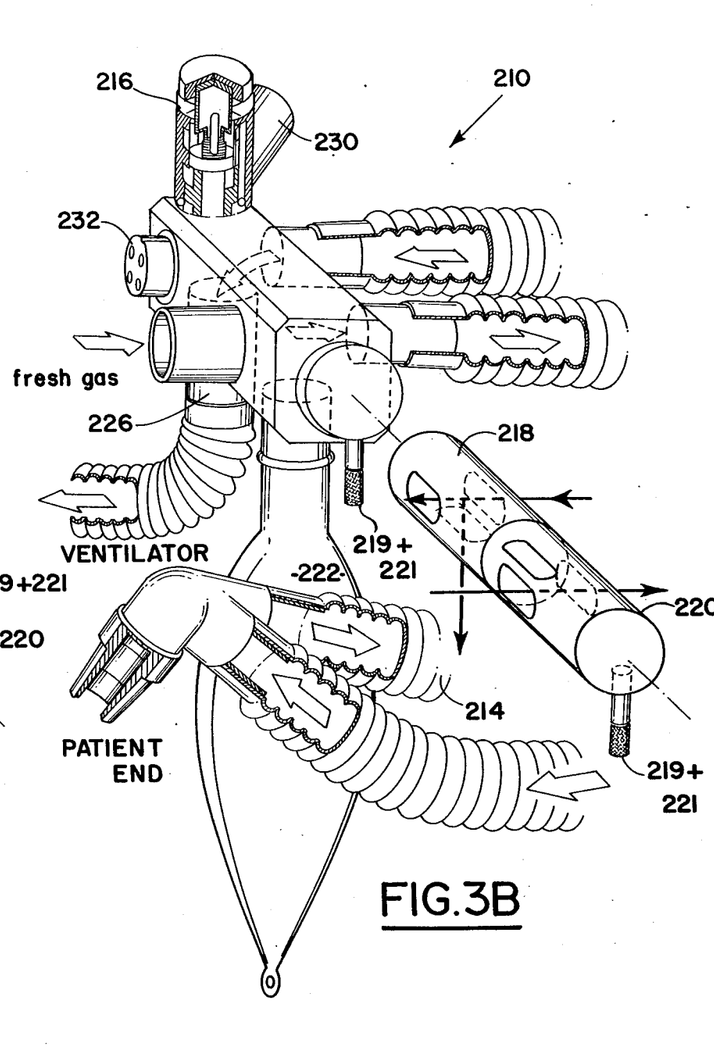

In FIG. 3 system 210 is similar to system 110 of FIG. 2 except that system 210 is shown in which the valves 218 (118 in FIG. 2) and 220 (120 in FIG. 2) have been physically but not functionally jointed into one unit. Levers 119 and 121 of FIG. 2 now share the same function, and hence in FIG. 3a a single lever has been shown as 219 and 221. An exploded view of valves 218 and 220 is shown in the respective positions for both spontaneous (FIG. 3a) and controlled ventilation (FIG. 3b). The flow characteristics and function remain identical to that of FIGS. 1 and 2. The bridge 233 has the same function as 133. A safety pressure release device 232 is shown attached to the distal end of the expiratory limb and can similarly be attached in place of cap 31 and 131 in FIGS. 1 and 2. The embodiments of FIGS. 1–3 may pertain in whole or in parts to other versions of the apparatus.

Figure 4:
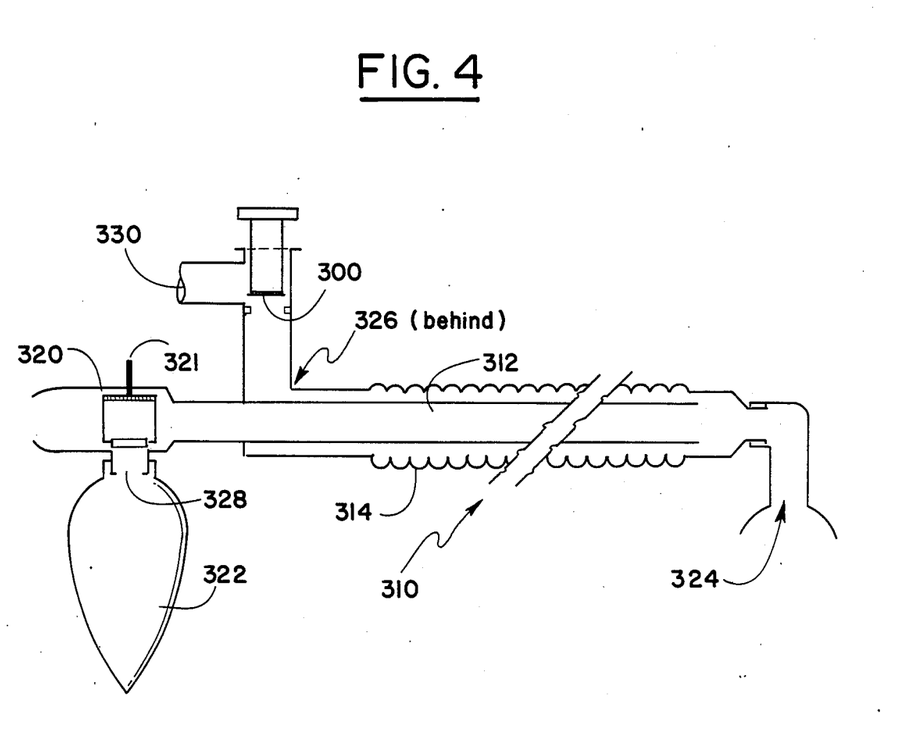
FIG. 4 is a sectional side-view of the invention in which the relief valve of the second outlet downstream of the first (not shown) is a screw-down valve. A coaxial tubing arrangement is shown.

In FIG. 4 the pop-off valve 16 in FIG. 1 (or 116 or 216) on the second expiratory outlet is replaced by a screwdown plunger valve 300. As the plunger is screwed down the valve offers increasing restriction to flow, and in this position during spontaneous respiration it functions similarly (but not quite as efficiently) to the pop-off valve 16 of FIG. 1 as described above for the preferred embodiment. In its fully open position valve 300 allows gases to flow freely through it; a ventilator may thus be directly attached to the valve instead of to the primary outlet 326. No difference in function occurs during controlled ventilation from that described for the preferred embodiment. Since the primary outlet 326 is no longer essential for the attachment of a ventilator, valve 18 of FIG. 1 may be omitted and outlet 326 used for the attachment of other apparatus such as a pressure-limiting relief valve or even closed off completely.

Figure 5:
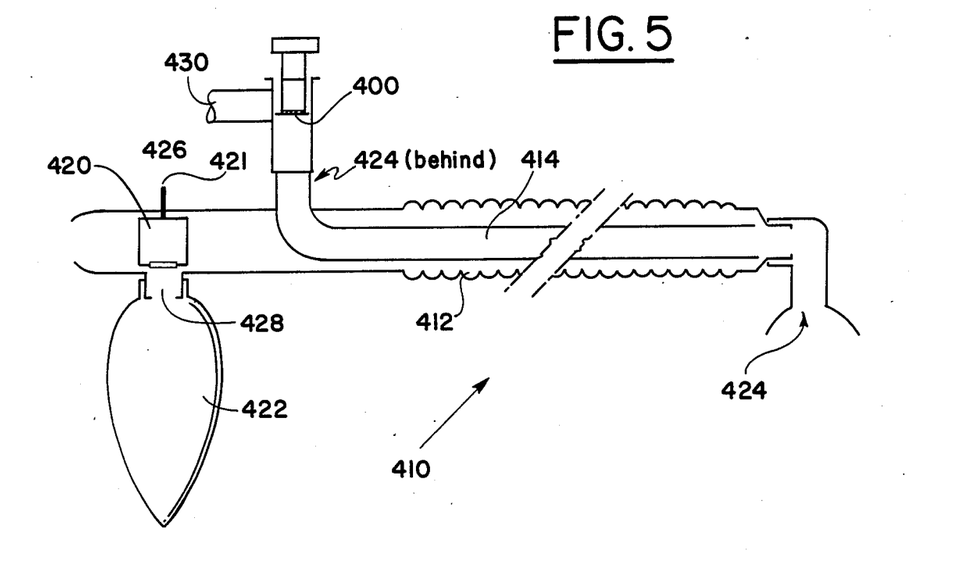
FIG. 5 is a sectional side-view of the invention in which the relief valve of the second outlet downstream of the first (not shown) is a screw-down valve. A coaxial tubing arrangement is shown in reverse to that in FIG. 4, the expiratory tube now being the inner of the coaxial tubes.

FIG. 5 is a reversal of the tubing configuration of FIG. 4, the expiratory tube 414 now being the inner of the co-axial tubes. The screw-down plunger valve 400 acts in the same manner as in FIG. 4.

Figure 6:
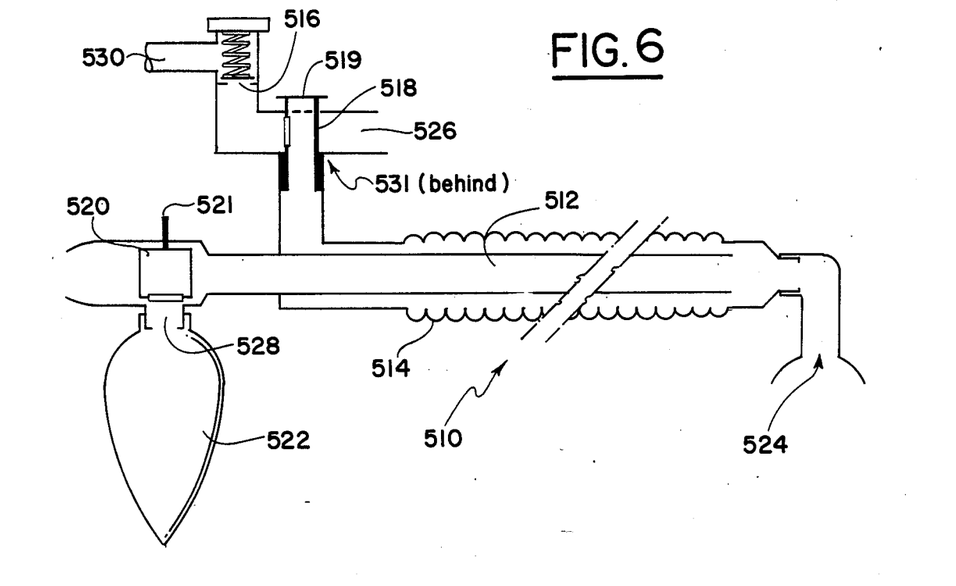
FIG. 6 is a diagrammatic sectional side-view of the invention in which the system in FIG. 1 is shown with the coaxial tubing reversed, such that the outer tube is now the expiratory tube.

FIG. 6 is likewise in reversal of the tubing configuration of FIG. 1, the expiratory tube 514 being the outer of the co-axial tubes.

Figure 7:
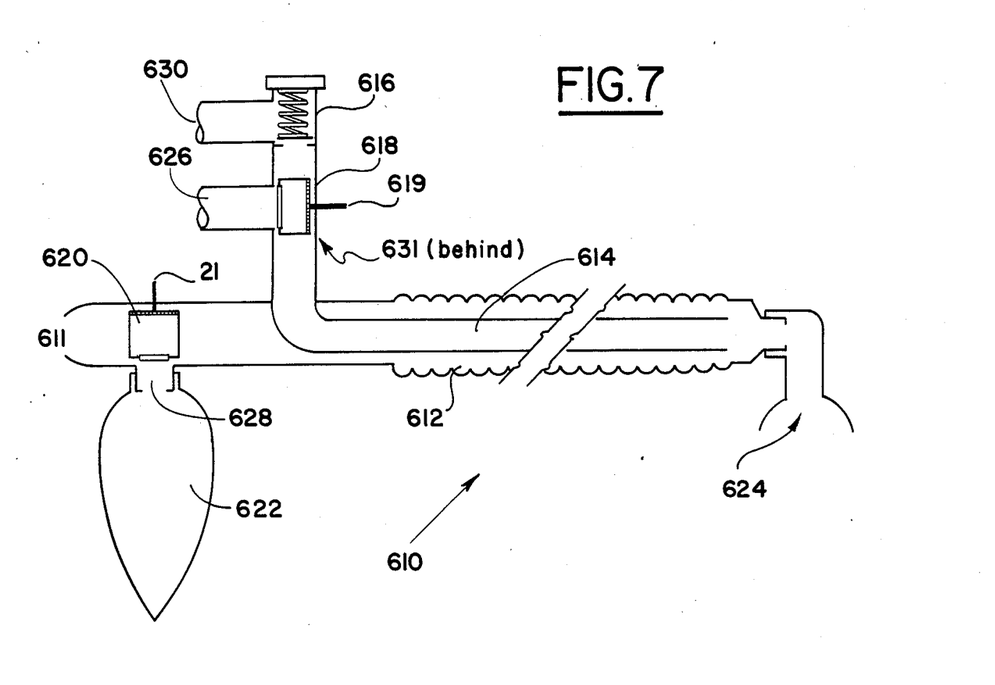
FIG. 7 is a diagrammatic sectional side-view of the invention in which the first outlet on the expiratory limb allows gas to flow to the second outlet in any position of the lever.

The apparatus drawn in FIG. 7 is essentially similar to that in FIG. 1. All components are identical, but valve 618 is so arranged so that in one position it allows gas to flow through relief valve 616 only, or in a second position through both the primary outlet 626 and relief valve 616. By allowing the relief valve 616 to be included during controlled ventilation, small amounts of ventilator gas can be leaked from the system thus enabling ventilators designed to give large volumes suitable only for adults to be used for children. The volume of gas reaching a child's lungs will depend on the degree of leak at valve 616 which is adjusted by the anaesthetist. The system described in FIG. 7 also allows the more conventional way of manually ventilating a patient to be used. A reservoir bag can be attached to the primary outlet 626 in place of the ventilator while gas is allowed to escape from the system in a controlled manner through valve 616 which is partially screwed down to prevent all gas escaping during inspiration. The system then functions as a Mapleson D system. Until the manual ventilation technique in the Mapleson A mode described above for the preferred embodiment has been independently confirmed to be efficient, safe, more practical and therefore acceptable, this D mode technique will remain the less controversial method.

Figure 8:
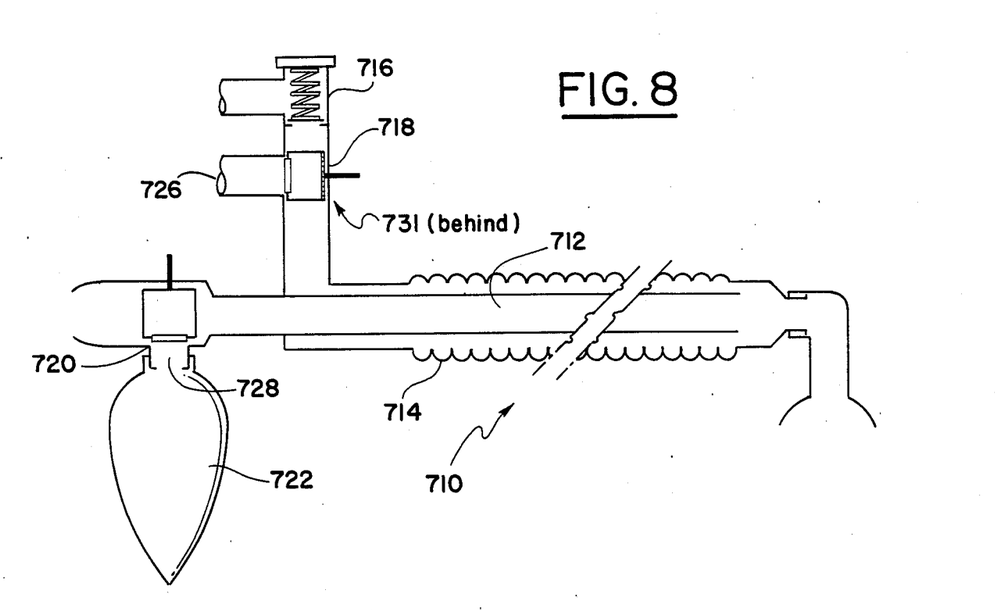
FIG. 8 is a diagrammatic sectional side-view of the invention in which the system in FIG. 7 is shown with the coaxial tubing reversed such that the outer tube now becomes the expiratory tube.

FIG. 8 is identical to FIG. 7 with the exception that the position of the coaxially arranged inspiratory and expiratory limbs are reversed in an identical manner to that described between FIGS. 4 and 5. A parallel non-coaxial version as in FIGS. 2 and 3 also pertain to this and other embodiments of the system.

It will be appreciated that the inspiratory and expiratory tubes in FIGS. 1–8 may lie in configurations other than those illustrated in each drawing. Furthermore a soda lime canister may be incorporated with two one-way valves and appropriate flexible tubing (if any) inserted near the expiratory outlet 26 in FIG. 1 (or 126, 226, 326, 426, 526, 626 or 726) and port 28 (or 128, 228, 328, 428, 528, 628 or 728). The flow of gases through the one-way valves will carry expired gases from the expiratory limb 14 (or 114, 214, 314, 414, 514, 614 or 714) towards the inspiratory limb 12 (or 112, 212, 312, 412, 512, 612 or 712).

It will also be appreciated from the above drawings and description that the method of control of valves 16 (or 116, 216, 300, 400, 516, 616 & 716), 18 (or 118, 218, 518, 618 & 718) and 20 (or 120, 220, 320, 420, 520, 620 & 720) is immaterial to function. Valve 18 and 20 of FIG. 1 or their counterparts in other Figures may be controlled by separate levers, by a single lever or by any other means whether operated by hand or other power source. Further, while valve 18 and 20 must be functionally distinct, they need not necessarily be physically separated. Alternative methods of physically combining the valves 18 and 20 to that shown in FIG. 3 are possible and will result in functionally identical systems to any one of the embodiments described.

In all the described embodiments of the system it will be noticed that reverse flow of ventilation gas back along the inspiratory limb can be prevented from reaching the reservoir bag when using a ventilator. If ventilation gas was permitted to reach the bag, ventilation of the reservoir bag would occur preferentially to the patient's lungs with potentially disasterous results. It follows that the function of valve 20 need only achieve this effect and therefore need not necessarily be a plug valve. While the latter is the most suitable, other valves such as a simple flap or one-way could be inserted into the inspiratory limb close to the reservoir bag such that reverse flow into this limb and the reservoir bag is prevented during controlled ventilation and yet allow both spontaneous and manual respiration.

It is also noted that valve 16 (or 116, 216, 300, 400, 516, 616 or 716) may be a simple spring-loaded or screw-down device, but the attachment of more complicated valves, some of which do not require manual adjustment, may be equally useful.

I claim:

1. An anaesthetic system comprising:
   (a) an inspiratory low pressure fresh gas supply tube having means for connection to a low pressure fresh gas supply,
   (b) said inspiratory tube including a reservoir bag connected near the inlet end of the tube through an adjustable valve,
   (c) an expiratory tube having outlet means for exhausting expiratory gas from the expiratory tube consisting of two outlets, the first outlet controlled by a valve means for allowing expiratory gas to exit the expiratory tube upstream from the second outlet which is controlled by a relief valve,
   (d) said inspiratory and expiratory tubes communicating with each other and being substantially free of restricted flow adjacent to a patient's face piece.

* * * * *